United States Patent
Stephens et al.

(10) Patent No.: US 6,457,365 B1
(45) Date of Patent: Oct. 1, 2002

(54) METHOD AND APPARATUS FOR ULTRASONIC IMAGING

(75) Inventors: Douglas N. Stephens, Davis, CA (US); Matthew O'Donnell, Ann Arbor, MI (US)

(73) Assignee: EndoSonics Corporation, Rancho Cordova, CA (US)

( * ) Notice: Subject to any disclaimer, the term of this patent is extended or adjusted under 35 U.S.C. 154(b) by 0 days.

(21) Appl. No.: 09/501,106

(22) Filed: Feb. 9, 2000

(51) Int. Cl.⁷ .............................. G01N 29/24; A61B 8/12
(52) U.S. Cl. .............................. 73/626; 73/628; 73/641; 600/447; 600/459; 600/462; 600/463; 600/466; 600/472
(58) Field of Search ........................... 73/620, 624, 625, 73/626, 627, 628, 641; 600/437, 440, 441, 443, 444, 447, 450, 453, 459, 462, 463, 466, 467, 468, 469, 472

(56) References Cited

U.S. PATENT DOCUMENTS

| | | | | |
|---|---|---|---|---|
| 4,915,115 A | * | 4/1990 | Sasaki et al. | 600/441 |
| 5,273,045 A | * | 12/1993 | Chihara et al. | 600/447 |
| 5,335,663 A | * | 8/1994 | Oakley et al. | 600/459 |
| 5,603,327 A | * | 2/1997 | Eberle et al. | 29/25.35 |
| 5,606,975 A | * | 3/1997 | Liang et al. | 600/437 |
| 5,651,336 A | * | 7/1997 | Rygiel et al. | 123/90.16 |
| 5,757,727 A | | 5/1998 | Hanafy et al. | 310/334 |
| 5,797,849 A | * | 8/1998 | Vesely et al. | 600/461 |
| 5,823,962 A | * | 10/1998 | Schaetzle et al. | 310/366 |
| 5,876,345 A | | 3/1999 | Eaton et al. | 600/466 |
| 5,906,580 A | * | 5/1999 | Kline-Schoder et al. | 310/334 |

FOREIGN PATENT DOCUMENTS

| | | |
|---|---|---|
| EP | 0 696 435 A2 * | 2/1996 |
| EP | 0 853 919 | 7/1998 |
| JP | 62 152441 | 12/1996 |
| WO | WO 93/08863 * | 5/1993 |

OTHER PUBLICATIONS

Notification of Transmittal of the International Search Report or the Declaration in the corresponding PCT Application No. PCT/US01/03894, dated Jul. 27, 2001.
Invitation to Pay Additional Fees including Annex to Form PCT/ISA/206 in corresponding PCT Application No. PCT/US01/03894, dated May 22, 2001.
Patent Abstracts of Japan, vol. 1995, No. 08 and JP 07 136164 A (Olympus Optical Co. Ltd. (as cited in CA above; PCT Annex to Form PT/ISA/206 above).
Busse, L.J., Dietz, D.R., "Sparse Circular Array Methods, Performance, and Applications to Intravascular Imaging," Proceedings of the 1991 IEEE Ultrasonics Symposium 91CH3079–1, pp. 641–544, 1991.
Norton, S.J., "Acoustical holography with an annular aperture," J. Acoust. Soc. America 71, pp. 1169–1178, 1982.
Evans, J.L., et al, "Arterial Imaging with a New Forward-Viewing Intravascular Ultrasound Catheter, I—Initial Studies," Circulation, vol. 89, No. 2, Feb. 1994, pp. 712–717.

(List continued on next page.)

Primary Examiner—Hezron Williams
Assistant Examiner—Rose M. Miller
(74) Attorney, Agent, or Firm—Leydig, Voit & Mayer, Ltd.

(57) ABSTRACT

An ultrasound transducer array (408) includes at least one transducer element (412) having a first (604) and second (606) portions separated by an acoustical discontinuity (520). The first portion (604) has the desired length to form a half-wave k31 resonance, while the second portion (606) has a resonant length for an undesired very low frequency out-of-band k31 resonance. The thickness of the transducer element (412) is designed for k33 half-resonance. Given the design, the transducer element (412) can operate and provide for both forward-looking (514) and side looking (512) elevation apertures. A method is also disclosed for using the disclosed ultrasound transducer (412) in ultrasound imaging.

27 Claims, 7 Drawing Sheets

OTHER PUBLICATIONS

Ng, K.H., et al, "Arterial Imaging With a New Forward-Viewing Intravascular Ultrasound Catheter, II—Three-Dimensional Reconstruction and Display of Data," Circulation, vol. 89, No. 2, Feb. 1994, pp. 718–723.

Liang, D.H., "A Forward–Viewing Intravascular Ultrasound Catheter Suitable for Intracoronary Use," Biomedical Instrumentation & Technology, Jan./Feb. 1997. pp. 45–53.

Moser, U., et al, "Benefits and Limitations of the C–Mode Doppler," Acoustical Imaging, vol. 21, 1995, pp. 509–514.

Schumacher, P.M., et al, "In Vitro Measurements of True Volume Flow with C–Mode Doppler," Acoustical Imaging, vol. 21, 1995, pp. 515–522.

Mehran, R., et al, "Treatment of In–Stent Restenosis with Excimer Laser Coronary Angioplasty." Circulation, vol. 96, No. 7, Oct. 1997, pp. 2183–2189.

Smith, S.W., et al, "High Speed Ultrasound Volumetric Imaging System—Part I: Transducer Design and Beam Steering," IEEE Transactions on Ultrasonics, Ferroelectrics, and Frequency Control, vol. 38, No. 2, Mar. 1991, pp. 100–108.

Lockwood, G.R., Foster, F.S., "Optimizing the Radiation Pattern of Sparse Periodic Two–Dimensional Arrays," IEEE Transactions on Ultrasonics, Ferroelectrics, and Frequency Control, vol. 43, No. 1, Jan. 1996, pp. 15–19.

Yock, P.G., Fitzgerald, P.J., "Intravascular Ultrasound: State of the Art and Future Directions," American Journal of Cardiology, Apr. 1998, vol. 81, No. 7A, pp. 27E–32E.

* cited by examiner

METHOD AND APPARATUS FOR ULTRASONIC IMAGING

TECHNICAL FIELD

This invention pertains generally to ultrasonic imaging and, more particularly, to an apparatus and method for ultrasonic imaging of small cavities with catheter based devices.

BACKGROUND

In recent years, intravascular ultrasound (IVUS) imaging systems have been designed for use by interventional cardiologists in the diagnosis and treatment of cardiovascular and peripheral vascular disease. Such systems enhance the effectiveness of the diagnosis and treatment by providing important diagnostic information that is not available from conventional x-ray angiography. This information includes the location, amount and composition of arteriosclerotic plaque and enables physicians to identify lesion characteristics, select an optimum course of treatment, position therapeutic devices and promptly assess the results of treatment.

Such IVUS systems generally include an IVUS device having one or more miniaturized transducers mounted on the tip of a catheter or guide wire to provide electronic signals to an external imaging system. The external imaging system produces an image of the lumen of the artery or other cavity into which the catheter is inserted, the tissue of the vessel, and/or the tissue surrounding the vessel. Problems encountered with these systems include clearly visualizing the tissue around the catheter, and identifying the precise location of the image with regard to known spatial references, such as angiographical references.

Some of the ultrasonic imaging catheters currently in use are "side viewing" devices which produce B-mode images in a plane which is perpendicular to the longitudinal axis of the catheter and passes through the transducer. That plane can be referred to as the B-mode lateral plane and is illustrated in FIG. 1. There are also "forward viewing" devices that produce a C-mode image plane as illustrated in FIG. 2 which is perpendicular to the axis of the catheter and spaced in front of the transducer. Other forward viewing devices produce a B-mode image in a plane that extends in a forward direction from the transducer and parallel to the axis of the catheter. That plane is referred to as the B-mode forward plane and is illustrated in FIG. 3. The forward viewing devices are particularly advantageous in that they allow the physician to see what is in front of the catheter, and they also allow imaging in areas which cannot be crossed with the catheter.

One problem with imaging catheters heretofore provided is that a given type of IVUS catheter can provide high quality images in only one of the mode planes. There are no known devices, for example, which can provide both B-mode forward imaging and C-mode imaging. As such there exists in the art a need for an ultrasonic imaging transducer and method of the above character which can overcome the limitations and disadvantages of the prior art as well as be able to provide images in multiple planes.

BRIEF DESCRIPTION OF THE DRAWINGS

The features of the present invention, which are believed to be novel, are set forth with particularity in the appended claims. The invention, together with further objects and advantages thereof, may best be understood by reference to the following description, taken in conjunction with the accompanying drawings, in the several figures of which like reference numerals identify like elements, and in which:

DETAILED DESCRIPTION OF THE PREFERRED EMBODIMENT

Figure 1:
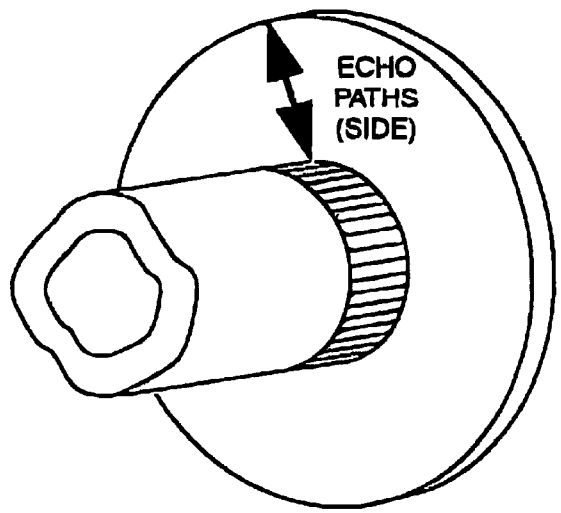
FIGS. 1–3 are isometric views showing different imaging planes generated by an ultrasonic catheter tip.

While the specification concludes with claims defining the features of the invention that are regarded as novel, it is believed that the invention will be better understood from a consideration of the following description in conjunction with the drawing figures, in which like reference numerals are carried forward.

Figure 4:
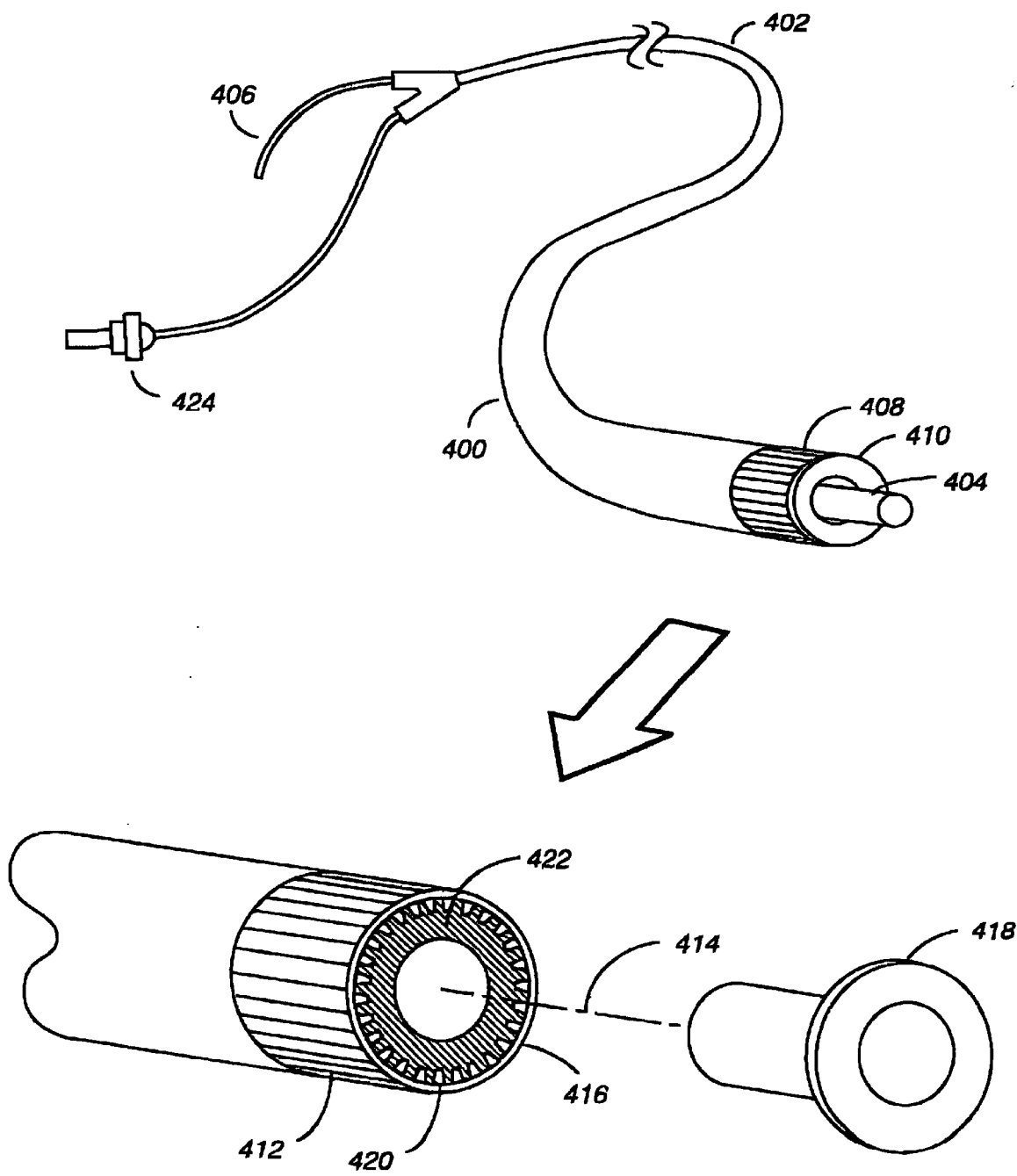
FIG. 4 is a drawing of one embodiment an ultrasonic imaging catheter with a guide wire and central distal lumen utilizing a ultrasonic transducer array assembly according to the present invention.

Referring now to FIG. 4, there is shown a catheter 400 for intravascular use. This catheter has an elongated flexible body 402 with an axially extending lumen 404 through which a guide wire 406, fluids, and/or various therapeutic devices or other instruments can be passed. The invention is not, however, limited to use with a catheter, and it can be utilized with any suitable catheter, guide wire, probe, etc. An ultrasonic imaging transducer assembly 408 is provided at the distal end 410 of the catheter, with a connector 424 located at the proximal end of the catheter. This transducer 408 comprises a plurality of transducer elements 412 that are preferably arranged in a cylindrical array centered about the longitudinal axis 414 of the catheter for transmitting and receiving ultrasonic energy.

The transducer elements 412 are mounted on the inner wall of a cylindrical substrate 416 which, in the embodiment illustrated, consists of a flexible circuit material that has been rolled into the form of a tube. The end portions 420 of the transducer elements 412 are shown at the distal portion of the transducer assembly. A transducer backing material 422 with the proper acoustical properties surrounds the transducer elements 412. An end cap 418, which isolates the ends of the transducer elements, is attached to the transducer assembly. Alternatively, the end portions 420 of the transducer elements 412 can be covered with nonconductive adhesive in order to insulate them from external fluids (e.g., blood).

Figure 5:
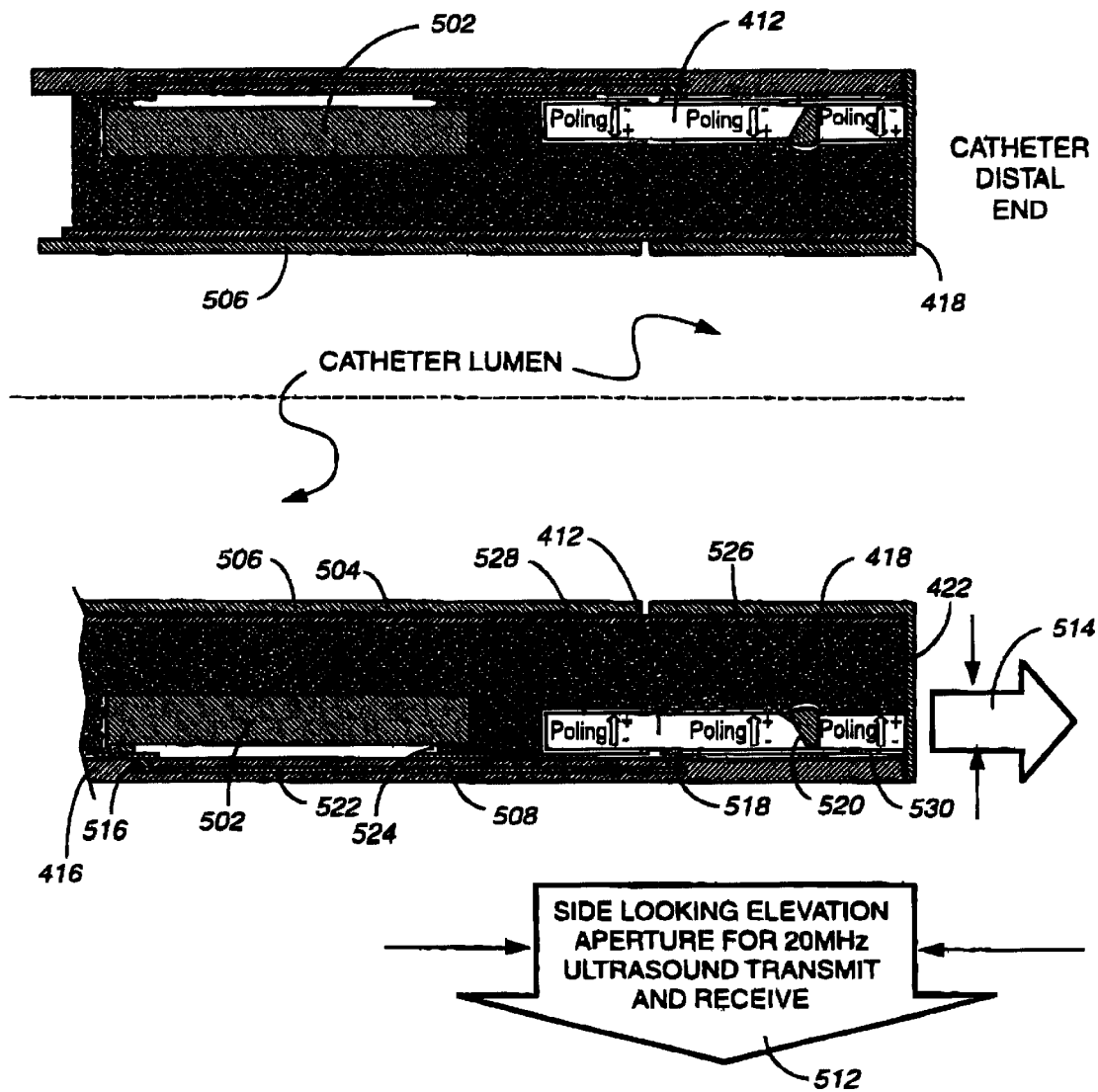
FIG. 5 is a side elevational view, partly broken away, showing one embodiment of an ultrasonic imaging catheter incorporating the invention.

In FIG. 5 there is shown a cross-sectional view of the transducer assembly 408 cut in half and showing both sides.

Integrated circuits 502 for interfacing with the transducer elements are mounted on the substrate 416 and interconnections between the circuits 502 and the transducer elements are made by electrically conductive traces 508 and 522 on the surface of the substrate and buried within it. Conductive trace 508 provides the "hot" conductor and interconnects the IC 502 to a transducer 412. Conductive trace 522 provides the ground conductor between the IC 502 and transducer 412. Interconnection vias 516, 518 and 524 provide electrical connections between the conductive traces 508, 510 and IC 502 and transducer element 512.

The transducer region has a central core that comprises a metal marker tube 504 and plastic members 506 and 418, one acting as a lining 506 to the lumen, and the other one is the end-cap piece 422 that acts both to protect the end of the catheter and to act as a type of acoustic coupling enhancement for ultrasound transmission out the end of the array. Between the central core of the catheter and the peripherally arranged array elements there is an acoustic absorbing material 422. The core has a cylindrical body with an annular end wall at its distal end and an axially extending opening that is aligned with the lumen in the catheter. A sleeve of metal 504 or other suitable radiopaque material is disposed coaxially about the core for use in locating the tip of the catheter within the body.

Each of the transducer elements 412 comprises an elongated body of PZT or other suitable piezoelectric material. The elements extend longitudinally on the cylindrical substrate and parallel to the axis of the catheter. Each element has a rectangular cross-section, with a generally flat surface at the distal end thereof. The transducer elements are piezoelectrically poled in one direction along their entire length as highlighted. A transversely extending notch 520 of generally triangular cross-section is formed in each of the transducer elements. The notch opens through the inner surface of the transducer element and extends almost all the way through to the outer surface. Preferably, the notch 520 has a vertical sidewall on the distal side and an inclined sidewall on the proximal side. The vertical wall is perpendicular to the longitudinal axis of the catheter, and the inclined wall is inclined at an angle on the order of 60° to the axis. The notch, which exists in all the array transducer elements, can be filled with a stable non-conductive material 526. An example of a material that can be used to fill notch 520 is a non-conductive epoxy having low acoustic impedance. Although not the preferred material, conductive materials having low acoustic impedance may also be used to fill notch 520. If a conductive material is used as the notch filler, it could avoid having to metalize the top portion to interconnect both portions of the transducer elements as required if a nonconductive material is utilized. Conductive materials are not the preferred notch filler given that they have an affect on the E-fields generated by the transducer elements.

In the preferred embodiment, the transducer array provides for a forward looking elevation aperture for 10 mega Hertz (MHz) ultrasound transmit and receive 514, and a side looking elevation aperture 512 for 20 MHz ultrasound transmit and receive. Other frequency combinations can be used depending on the particular design requirements. The inner and outer surfaces of the transducer elements are metallized to form electrodes 528, 530. A secondary metalization is formed over the insulated notch area 520 to create a continuous electrical connection of the electrode 530 between its proximal and distal ends. Outer electrode serves as a ground electrode 530 and is connected by means of metal via 518 to trace 522, which is buried in the substrate. Inner electrode 528 extends along the walls of notch 520, wraps around the proximal end of the element and is connected directly to trace 508 on the surface of the substrate. In one embodiment, the transducer metallization consists of a layer of gold over a layer of chrome, with the chrome serving as an adhesion layer for the gold. Those skilled in the art will realize that other metalization materials can be utilized.

Figure 8:
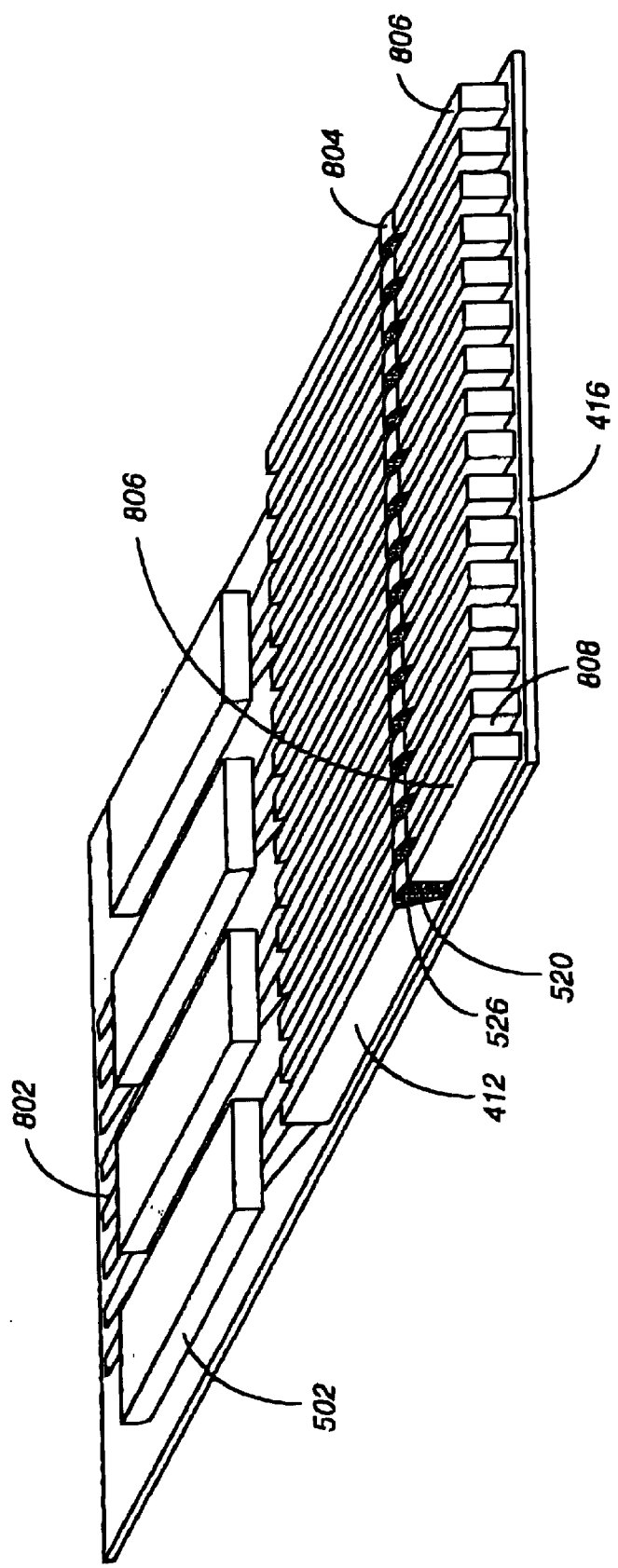
FIG. 8 is a diagram of an ultrasonic transducer array assembly shown during manufacturing in its flat state in accordance with the invention.

The transducer array is manufactured by electrically and mechanically bonding a poled, metallized block of the piezoelectric material 412 to the flexible circuit substrate 416 with the substrate in its unrolled or flat condition as shown in FIG. 8. The transducer block exists, as a piezoelectrically poled state where the thickness-axis poling is generally uniform in distribution and in the same axis throughout the entire block of material. Notch 520 is then formed across the entire piezoelectric block, e.g. by cutting it with a dicing saw. Each of the individual notches 520 is filled with a material 526 such as plastic and a metallization 804 is applied to the top of the notch to form a continuous transducer inner electrode with metallization 806. The block is then cut lengthwise to form the individual elements that are isolated from each other both electrically and mechanically, with kerfs 808 formed between the elements. Cable wire attachment terminals 802 are provided on the substrate which allow microcables that are electrically connected to an external ultrasound system to connect with the transducer assembly in order to control the transducers.

The integrated circuits 502 are installed on the substrate 416, and the substrate is then rolled into its cylindrical shape, with the transducer elements on the inner side of the cylinder. The sleeve of radiopaque material is mounted on the core, the core is positioned within the cylinder, and the acoustic absorbing material is introduced into the volume between the core and the transducer elements. In the event that a radiopaque marker is not required for a particular application, it can be omitted.

The transducer elements 412 can be operated to preferentially transmit and receive ultrasonic energy in either a thickness extensional TE) mode ($k_{33}$ operation) or a length extensional (LE) mode ($k_{31}$ operation). The frequency of excitation for the TE mode is determined by the thickness of the transducer elements in the radial direction, and the frequency for the LE mode is determined by the length of the body between distal end surface 614 and the vertical wall 610 of notch 520. The thickness TE mode is resonant at a frequency whose half wavelength in the piezoelectric material is equal to the thickness of the element. And the LE mode is resonant at a frequency whose half wavelength in the piezoelectric material is equal to the distance between the distal end and the notch. Each transducer element is capable of individually operating to transmit and receive ultrasound energy in either mode, with the selection of the desired mode (i.e. "side", or "forward") being dependent upon; a) an electronically selected frequency band of interest, b) a transducer design that spatially isolates the echo beam patterns between the two modes, and c) image plane specific beamforming weights and delays for a particular desired image plane to reconstruct using synthetic aperture beamforming techniques, where echo timing incoherence between the "side" and "forward" beam patterns will help maintain modal isolation.

Figure 6:
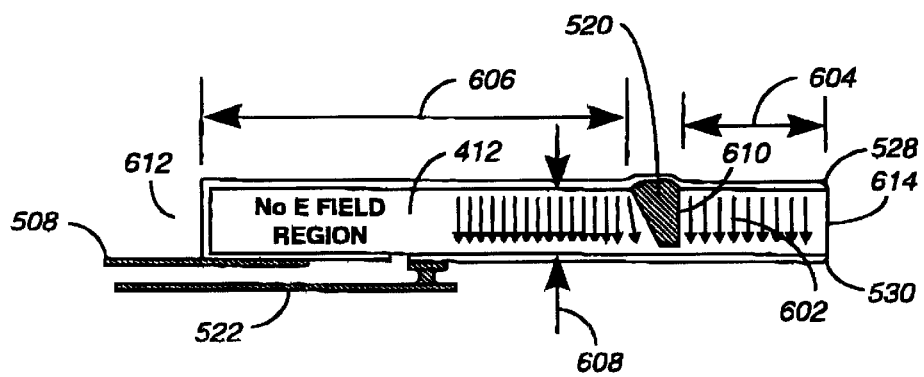
FIG. 6 is an enlarged sectional view of one embodiment of an ultrasonic transducer element in accordance with the invention.

In FIG. 6 there is shown an illustration of a transducer element 412 showing the E fields generated. In one presently preferred embodiment, the distance 604 between the notch 520 which forms an acoustical discontinuity and the distal end of each transducer element, also referred to as the first portion of the transducer element, is made equal to approximately twice the thickness 608 of the element, resulting in a resonant frequency for the TE mode that is approximately twice the resonant frequency for the LE mode. To assure good modal dispersion between the two modes, the TE frequency should be at least 1.5 times the LE frequency, and preferably at least twice. The steep wall 610 or sharp cut on the distal side of the notch provides an abrupt end to the acoustic transmission path in the piezoelectric material and facilitates a half wave resonant condition at the LE frequency of operation.

The transducer element segment or second portion 606 which is between the notch 520 and the proximal end 612 of the element will also be able to resonate in an LE mode, but the design, through careful selection of this segment length, can be made to place this resonant frequency (and its harmonics) at a low (or high) enough frequency to create a reasonable modal dispersion characteristic. The LE mode acoustic coupling for this segment to the "end" of the array will also be quite poor, and aid in attenuating its undesired response. This segment though may certainly participate in the TE mode excitation, to define the "side looking" aperture as the whole length of the piezoelectrically active element. Any element in the array can also be selectively used as a receiver of ultrasonic energy in either the TE or the LE mode of operation by the ultrasound system that is connected to the ultrasound assembly.

Figure 7:
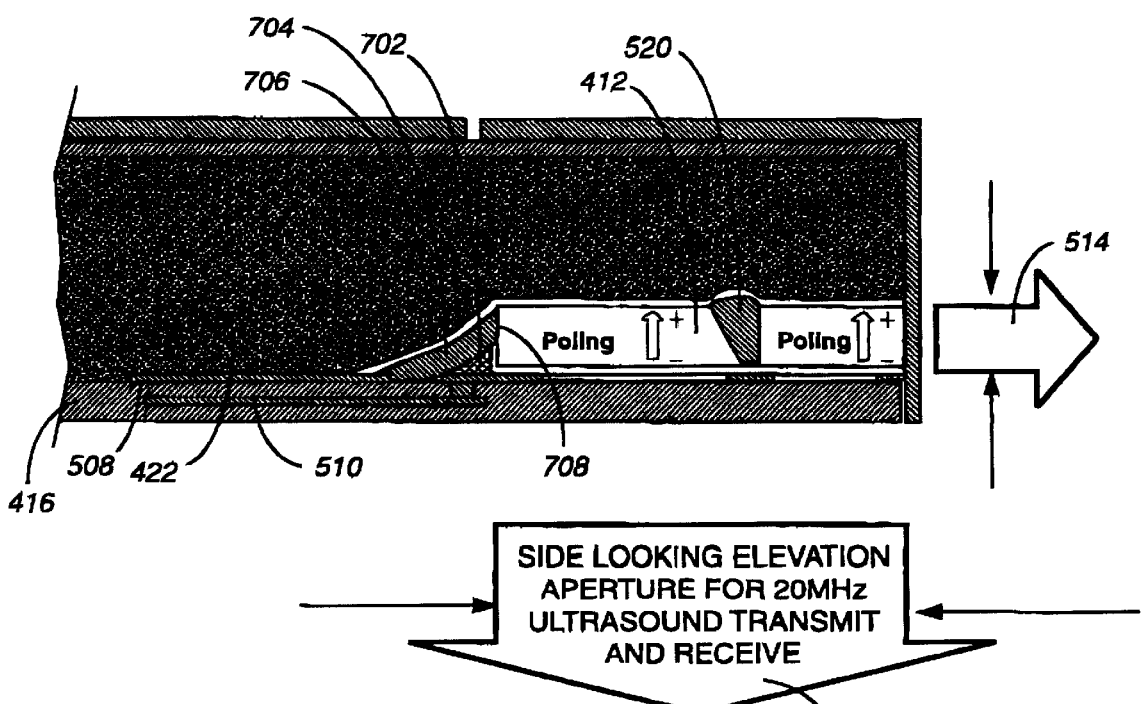
FIG. 7 is a side cross-sectional view of an alternate embodiment of a transducer element interconnection technique in accordance with the invention.

In FIG. 7 there is shown an alternate interconnection technique used to interconnect between the IC 502 and the individual transducer elements 412. In this embodiment a solder or other conductive material such as a metal-epoxy 702 is used to connect ground trace 510 with the ground electrode of the transducer element. An insulating separation layer 708 between the ground and "hot" electrodes is located at the proximal end of the transducer element 412. In order to connect the "hot" conductive trace or runner 508 to its corresponding electrode on the transducer element, epoxy insulation 704 is used. The top of the epoxy insulation is then metallized 706 in order to electrically interconnect the trace or runner 508 to its corresponding electrode prior to dicing the transducer block into discrete elements.

Multiple Modes of Imaging: Explanation of the Principals of Operation

A piezoelectric transducer, when properly excited, will perform a translation of electrical energy to mechanical energy, and as well, mechanical to electrical. The effectiveness of these translations depends largely on the fundamental transduction efficiency of the transducer assembly taken as a whole. The transducer is a three dimensional electromechanical device though, and as such is always capable of some degree of electromechanical coupling in all possible resonate modes, with one or several modes dominating. Generally an imaging transducer design seeks to create a single dominate mode of electromechanical coupling, suppressing all other coupling modes as "spurious." The common method used to accomplish a transducer design with a single dominate mode of electromechanical coupling usually rests in the creation of a single, efficient mechanical coupling "port" to the medium outside of the transducer. The single port is created by mounting the transducer such that the most efficient resonant mode of transducer operation faces that mechanical coupling port, with all other modes suppressed by means of mechanical dispersion attained by transducer dimensional control and dampening materials.

In the design of the present invention, the transducer design utilizes the fact that a transducer can be effective in two principal electromechanical coupling modes, each mode using a different frequency of operation, acoustic "port", and electro-mechanical coupling efficiency. One port is the "side looking" port that is used in the cross-sectional view image as shown in FIG. 1. The other port is the "end", or, "forward looking" port of the array.

The present invention allows the two electromechanical coupling modes (i.e. "side" 512 and "forward" 514) to be always active, without any mechanical switching necessary to choose one mode exclusive of the other. The design of this invention also assures that echoes of any image target in the "side looking" plane (see FIG. 1) do not interfere with the target reconstruction in the "forward looking" planes (see FIGS. 2 and 3), and reciprocally, image targets from the "forward looking" do not interfere with the target reconstruction in the "side looking" planes. In accordance with the invention, the design methods listed below are used to maintain sufficient isolation between the two modes of operation.

A) Resonant and Spatial Isolation of the Two Modes

The "side looking" port is designed for approximately twice the frequency of the "forward looking" port in accordance with the preferred embodiment. The transducer dimensional design is such that the "high frequency and side looking" transducer port sensitivity to low frequency signals, and as well the "low frequency and forward looking" transducer port to high frequency signals, is very low.

Additionally, the transmit and receive acoustic "beam" directions of the two modes 512 and 514 are at approximately right angles to each other and this feature offers an additional isolation with respect to image target identification. Also, as a means to further promote isolation between the two modes of operation, and as well optimize a sparse array echo collection method, the echo collection process in "forward" beam reconstruction uses an intentional physical separation of transmitting and receiving transducer elements of preferably 10 elements or more in the circular array annulus. This physical separation aids in preventing "spurious" transmit echoes from the "high frequency side looking" port from contaminating the receiving element listening to "forward only" echoes at the its lower frequency of operation.

B) Electrical Frequency Band Isolation of the Two Modes

As stated previously, the two modes of operation are operated at center frequencies that differ by about a factor of two. This design feature allows for additional isolation between the two modes through the use of band pass filters in the host system that is processing the echo signals received from the catheter. Additionally, if one or both of the two modes is operated in a low fractional bandwidth design (i.e. <30%), the bandpass filters will be even more effective in the maintenance of very high modal isolation.

C) Beam Formation Isolation Through Synthetic Aperture Reconstruction

Synthetic aperture beam reconstruction is used for all image modes. The beam formation process will preferentially focus only on image targets that are coherently imaged in a particular image plane. Thus, while image reconstruction is forming an image in, for example, the "side looking" plane, targets that may have contaminated the echoes from the "forward looking" planes will be generally incoherent and will be suppressed as a type of background noise. The reciprocal is also true: "side looking" echoes contaminants will be generally incoherent in "forward looking" imaging and will be suppressed through the process of synthetic aperture reconstruction.

A flexible digital image reconstruction system is required for the creation of multiple image planes on demand. The preferred method of assembling multiple image planes utilizes a synthetic aperture reconstruction approach. The "side looking" image shown in FIG. 1 can be reconstructed using sampled transducer element apertures as large as for example 14 contiguous transducer elements in a 64 total transducer element circular array. The transmit-receive echo collection for aperture reconstruction can be continuously shifted around the circular array, sampling all transmit-receive cross-product terms to be used in a particular aperture reconstruction. Within any 14-element aperture there can be 105 independent transmit-receive echo cross products used to construct the image synthetically.

Figure 2:
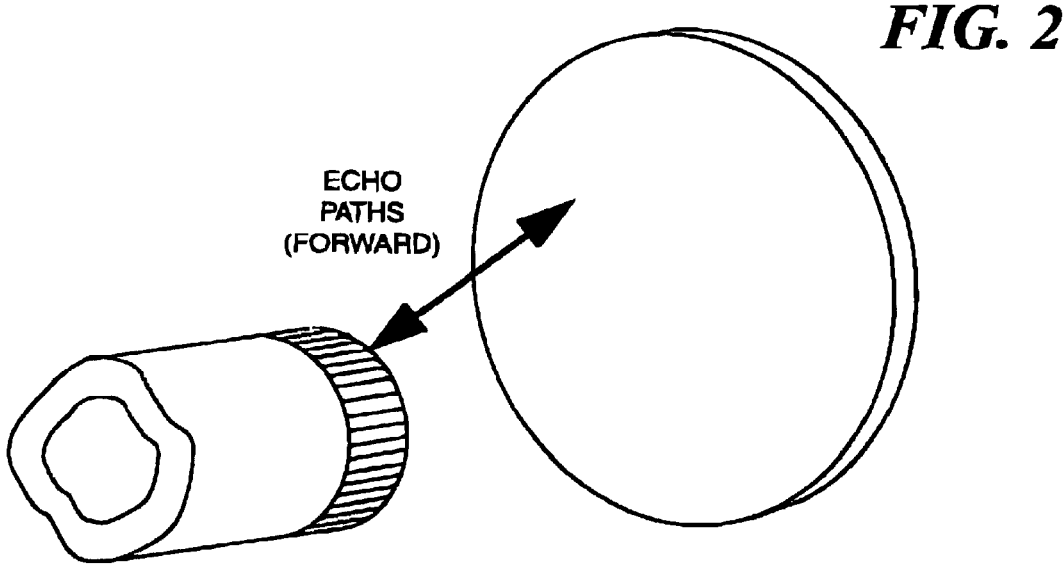
Figure 3:
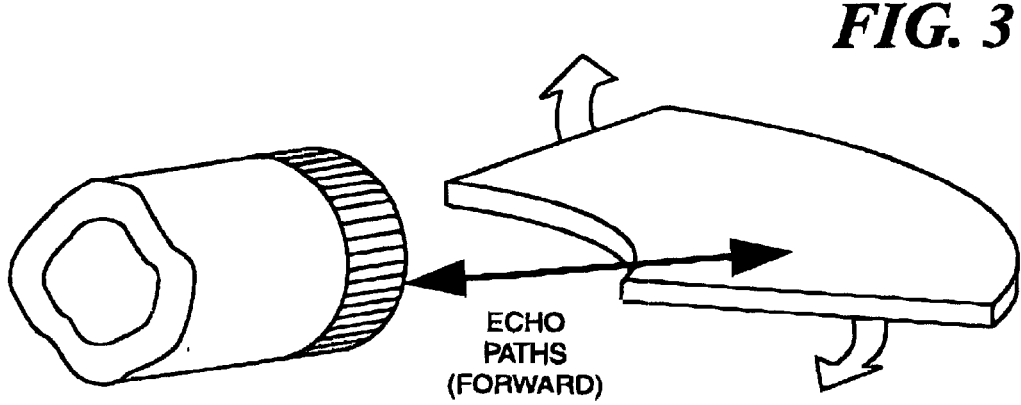

"Forward looking" images shown in FIGS. 2 and 3 can be reconstructed using sampled apertures that consist of selected transducer elements arranged on the annulus end of the circular array. For the 64 transducer element example mentioned above, all elements may contribute to a complete data set capture (this would consist of 64 by 32 independent transmit-receive element cross-products) to form a "forward looking" image in either C-mode or B-mode. As an alternative to the complete data set approach, a reduced number of independent transmit-receive element cross-products are used to adequately formulate the image. The transmit-receive echo collection for aperture reconstruction can be continuously shifted around the circular array, sampling all transmit-receive element cross-products to be used in a particular aperture reconstruction.

Special signal processing may be advantageous, especially in the "forward looking" imaging modes that use a less efficient transducer coupling coefficient ($k_{31}$) and as well may suffer from additional diffraction loss not experienced in the "side looking" mode of synthetic aperture imaging. In forming a "forward looking" C-mode image plane as an example, a low noise bandwidth can be achieved by using a high number of transmit pulses and a narrow bandpass echo filter in the processing system. Additionally, or as a preferred alternative, a matched filter implementation from the use of correlation processing may be used to improve the echo signal-to-noise ratio.

Standard Cross-Sectional B-Mode Operation

The advantage of this cross-sectional B-mode operation of the catheter imaging device is in its ability to see an image at great depth in the radial dimension from the catheter, and at high image resolution. This depth of view can help aid the user of the catheter to position the device correctly prior to electronically switching to a "forward viewing" mode of operation. Image targets moving quickly in a path generally parallel to the long axis of the catheter can be detected and displayed as a colored region in this mode; this information can be used to compare and confirm moving target information from the "forward viewing" mode of operation of the catheter to enhance the usefulness of the imaging tool.

1. Transducer Operation

The transducer in this "primary" mode operates in the thickness extensional (TE) resonance, utilizing the $k_{33}$ electro-mechanical coupling coefficient to describe the coupling efficiency. This "thickness resonance" refers to a quarter wave or half wave (depending on the acoustic impedance of the transducer backing formulation) resonance in the transducer dimension that is in alignment with the polarization direction of the transducer, and also the sensed or applied electric field. This TE mode utilizes a typically high frequency thickness resonance developed in the transducer short dimension following either electric field excitation to generate ultrasound acoustic transmit echoes, or, in reception mode following acoustic excitation to generate an electric field in the transducer.

Array Stepping

The TE mode is used for generating a cross-sectional B-mode image. This cross-section image cuts through the array elements in an orthogonal plane to the long axis of the transducer elements. Echo information gathered from sequential transducer element sampling around the array allows for the synthetically derived apertures of various sizes around the array. For the creation of any synthetically derived aperture, a contiguous group of transducer elements in the array are sequentially used in a way to fully sample all the echo-independent transmit-receive element pairs from the aperture. This sequencing of elements to fully sample an aperture usually involves the transmission of echo information from one or more contiguous elements in the aperture and the reception of echo information on the same or other elements, proceeding until all the echo independent transmit-receive pairs are collected.

Notch Effect

The small notch (520) forming an acoustical discontinuity in the middle of the array will have a minor, but insignificant effect on the TE mode transmission or reception beam pattern for that element. The small notch will be a non-active region for the TE mode resonance and therefore contribute to a "hole" in the very near field beam pattern for each element. The important beam characteristics however, such as the main lobe effective beam width and amplitude, will not be substantially effected, and except for a very minor rise in the transducer elevation side lobes, reasonable beam characteristics will be preserved as if the entire length of the transducer element was uniformly active.

Modal Dispersion

The TE mode transducer operation will exist with other resonant modes simultaneously. The efficiency of electro-mechanical energy coupling however for each mode though depends on primarily these factors: a) the k coefficient that describes the energy efficiency of transduction for a given resonance node, b) the acoustic coupling path to the desired insonification medium, and c) the echo transmission-reception signal bandwidth matching to the transducer resonance for that particular mode. Thus, for the creation of a "side looking" image, a transducer design is created to optimize the factors above for only the TE resonance, while the other resonant modes within a transducer are to be ignored through the design which suppresses the undesired resonances by minimizing the energy coupling factors mentioned above.

Through this frequency dispersion of unwanted coupling, the desired echoes transmitted and received from the "side looking" transducer port necessary to create a B-mode image plane will be most efficiently coupled through the TE resonance mode within any particular element. Therefore, the proposed transducer design which features a high efficiency TE mode coupling for desired echoes and frequency dispersion of the unwanted resonances and echoes, along with the other modal isolation reasons stated in an earlier section, constitutes a means for high quality TE echo energy transduction for only those desired in-plane echoes used in the creation of the B-mode cross-sectional image plane.

2. System operation for the Standard Cross-Sectional B-Mode Imaging

Figure 9:
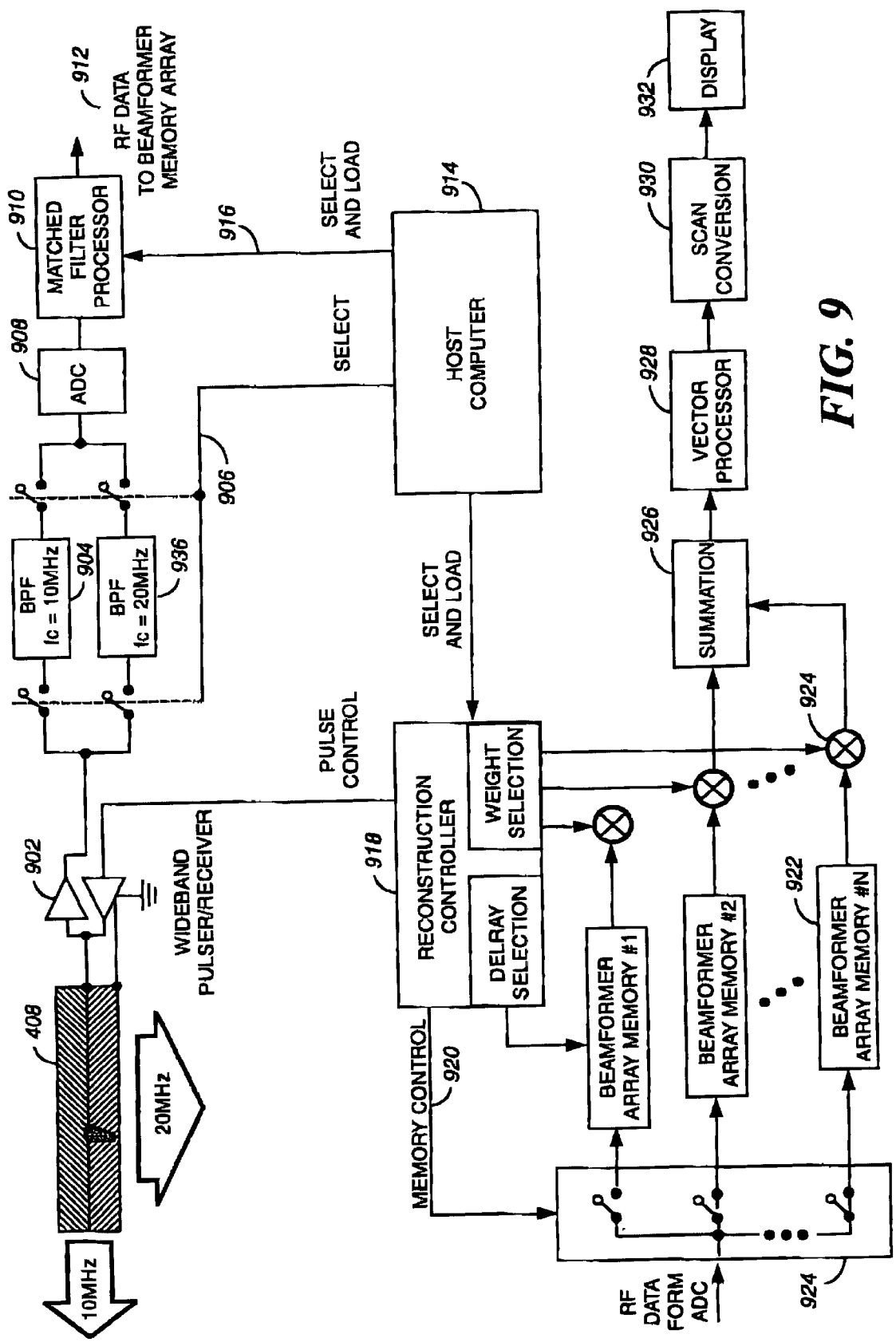
FIG. 9 shows a block diagram of an ultrasound system in accordance with the present invention.

The host ultrasound processing system shown in FIG. 9 controls the ultrasound array 408 element selection and stepping process whereby a single element 412 or multiple elements will transmit and the same or other elements will receive the return echo information. The elements in the array that participate in a given aperture will be sampled sequentially so that all essential cross product transmit-receive terms needed in the beam forming sum are obtained.

The host processing system or computer 914 and reconstruction controller 918 will control the transmit pulse timing provided to wideband pulser/receiver 902, the use of any matched filter 910 via control line 916 to perform echo pulse compression. The echo band pass filter (BPF) processing paths in the system are selected using control signal 906 to select between either the 10 MHz 904 or 20 MHz 936 center frequency BPF paths. The amplified and processed analog echo information is digitized using ADC 908 with enough bits to preserve the dynamic range of the echo signals, and passed to the beamformer processing section via signal 912. The beam former section under the control of reconstruction controller 918 uses stored echo data from all the transmit-receive element pairs that exist in an aperture of interest. As the element echo sampling continues sequentially around the circular array, all element group apertures are "reconstructed" using well known synthetic aperture reconstruction techniques to form beamformed vectors of weighted and summed echo data that radially emanate from the catheter surface using beamformer memory array 922, devices 924 and summation unit 926. Memory control signal 920 controls switch bank 924 which selects which memory array to store the incoming data.

The vector echo data is processed through envelope detection of the echo data and rejection of the RF carrier using vector processor 928. Finally a process of coordinate conversion is done to map the radial vector lines of echo data to raster scan data using scan converter 930 for video display using display 932.

This processing system, through the host control, may also accomplish a blood velocity detection by tracking the blood cells through the elevation length of the transducer beams. The tracking scheme involves a modification of the element echo sampling sequencing and the use of the beamformer section of the host processing system. The blood velocity information may be displayed as a color on the video display; this blood velocity color information is superimposed on the image display to allow the user to see simultaneous anatomical information and blood movement information.

Forward Looking Cross-Sectional C-Mode Operation

The advantage of this "forward looking" operation of the catheter imaging device is in its ability to see an image of objects in front of the catheter where possibly the catheter could not otherwise physically traverse. A "forward" C-mode plane produces a cross-sectional view similar to the standard B-mode cross-sectional view, and so can offer comparable image interpretation for the user, and as well this forward image plane is made more useful because the user can see the presence of image targets at the center of the image, otherwise obscured in the standard cross-sectional view by the catheter itself. This forward view allows also the ideal acoustic beam positioning for the detection and color image display of Doppler echo signals from targets moving generally in parallel with the long axis of the catheter device.

1. Transducer Operation

The transducer in this "secondary" mode operates in the length extensional (LE) resonance, utilizing the $k_{31}$ electromechanical coupling coefficient to describe the coupling efficiency. In this mode of operation, the poling direction of the transducer element and the sensed or applied electric field in the transducer are in alignment, but the acoustic resonance is at 90 degrees to the electric field and poling direction. This "length resonance" refers fundamentally to a half wave resonance in the transducer element's length dimension that is at 90 degrees with the polarization direction of the transducer. The LE mode of resonance, which is typically much lower in resonant frequency than the TE mode because the element length is normally much longer than the thickness dimension, always exists to some extent in a typical transducer array element, but is usually suppressed through a frequency dispersive design.

The preferred embodiment of the present invention utilizes an abrupt physical discontinuity (a notch 520) in the transducer element to allow a half wave LE resonance to manifest itself at a desired frequency, in the case of the preferred embodiment, at about one half the frequency of the TE mode resonance. A unique feature of this invention is a mechanically fixed transducer design that allows two resonant modes to operate at reasonably high efficiencies, while the "selection" of a desired mode (i.e. "side", or "forward") is a function of a) an electronically selected frequency band of interest, b) a transducer design that spatially isolates the echo beam patterns between the two modes, and c) image plane specific beamforming weights and delays for a particular desired image plane to reconstruct using synthetic aperture beamforming techniques, where echo timing incoherence between the "side" and "forward" beam patterns will help maintain modal isolation.

As discussed earlier, a resonant mode in a transducer design can be made efficient in electromechanical energy coupling if at least the three fundamental factors effecting coupling merit are optimized, namely a) the k coefficient (in this case it is the $k_{31}$ electro-mechanical coupling coefficient) that describes the energy efficiency of transduction for a given resonance node, b) the acoustic coupling path to the desired insonification medium, and c) the echo transmission-reception signal bandwidth matching to the transducer resonance for that particular mode. The invention allows for reasonable optimization of these factors for the LE mode of resonance, although the LE mode coupling efficiency is lower than that of the TE mode coupling. The $k_{31}$ coupling factor, used in describing LE mode efficiency, is typically one half that of $k_{33}$, the coupling factor that describes the TE mode efficiency.

The abrupt acoustical discontinuity in the transducer element is created at a step in the assembly of the array. Following the attachment of the transducer material to the flex circuit to create a mechanical bond and electrical connection between the transducer block and the flex circuit, while the transducer material is still in block form, a dicing saw cut can be made the entire length of the transducer material block, creating the notch. The notch depth should be deep enough in the transducer material to create an abrupt discontinuity in the distal portion of the transducer material to allow for a high efficiency LE mode half wave resonance to exist in this end of the transducer element. The saw cut should not be so deep as to sever the ground electrode trace on the transducer block side bonded to the flex circuit. The cut should ideally have a taper on the proximal side to allow for acoustically emitted energy to be reflected up into the backing material area and become absorbed.

It is not desirable that any acoustic coupling exist between the LE modes of resonance in the distal and proximal transducer regions separated by the notch. The distal transducer region LE mode half wave resonance will exist at 10 MHz in PZT (Motorola 3203HD) for a length of about 170 microns between the distal end of the transducer element and the notch. The proximal transducer region LE mode resonance will exist at a frequency considered out of band (approximately 6 MHz) in the two embodiments shown in FIGS. 5 and 7 so as to minimally interfere with the desired operating frequencies (in this case 10 MHz LE mode resonance in the distal region for "forward" acoustic propagation, and 20 MHz TE mode resonance in the entire active field length of the transducer).

The desired acoustic energy coupling port of the distal transducer LE resonant mode region is at the distal end of the catheter array. To protect the end of the array and potentially act as an acoustic matching layer, an end cap made of polyurethane could be used, or alternatively, a uniform coating of adhesive material would suffice. The beam pattern produced by this acoustic port must be broad enough to insonify a large area that covers intended extent of the image plane to be formed. To this end, the beam pattern must typically be at least 60 degrees wide as a "cone shaped" beam measured in the plane to be formed at the half-maximum intensity angles for 2-way (transmitted and received) echoes. The preferred design of the array has 64 or more elements, and a transducer sawing pitch equal to pi times the catheter array diameter divided by the number of elements in the array. For an effective array diameter of 1.13 mm and 64 elements, the pitch is 0.055 mm. Using two consecutive array elements as a "single" effective LE mode acoustic port can provide an adequate, uniform beam pattern that produces the required 60-degree full-width half maximum ("FWHM") figure of merit. The aperture of this "single" forward looking port is then approximately 0.080 mm by 0.085 mm (where 0.085 mm is twice the pitch dimension minus the kerf width of 0.025 mm).

The transducer design may also include a version where no notch is needed in the transducer block. In this case, the driven electrode can exist all along one surface of the transducer element, and the ground or reference electrode can exist all along the opposite side of the element. The long axis length of the transducer will resonate at a half wavelength in LE mode, and the thickness dimension will allow the production of a TE mode resonance in that thickness dimension. In order for this design to operate though, the LE and TE mode resonant frequencies will be quite different in order to maintain the proper TE mode elevation beam focus. As an example, in maintaining the length of the active region of the element for an adequately narrow 20 MHz TE mode elevation beam width at 3 mm radially distant from the catheter, the element length should be approximately 0.5 mm long. The resulting half wave resonance frequency in LE mode then will be about 3 MHz. This design can be used for dual-mode imaging, but will not offer the focusing benefits that 10 MHz imaging can offer for the forward looking image planes. Other designs are possible, where the forward frequency is maintained near 10 MHz, but the required frequency for the side-looking mode will rise dramatically, and although this can be useful in itself, will complicate the design by requiring a concomitant increase in the number of elements and/or a reduction in the array element pitch dimension.

2. System Operation

The host processing system will control the array element selection and stepping process whereby one element, a two element pair, or other multiple elements in combination, will transmit and the same or other elements will receive the return echo information. The intended array operational mode is the LE resonant mode to send and receive echo information in a forward direction from the end of the catheter array. As stated earlier, the LE mode echoes produced may be isolated from the TE mode echoes through primarily frequency band limitations (both by transducer structural design and by electrical band selection filters), and through the beamforming reconstruction process itself as a kind of echo selection filter.

To produce an image of the best possible in-plane resolution while operating in the forward-looking cross-sectional C-mode, the entire array diameter will be used as the maximum aperture dimension. This means that, in general, element echo sampling will take place at element locations throughout the whole array in preferably a sparse sampling mode of operation to gather the necessary minimum number of cross-product echoes needed to create image resolution of high quality everywhere in the reconstructed plane.

Figure 10:
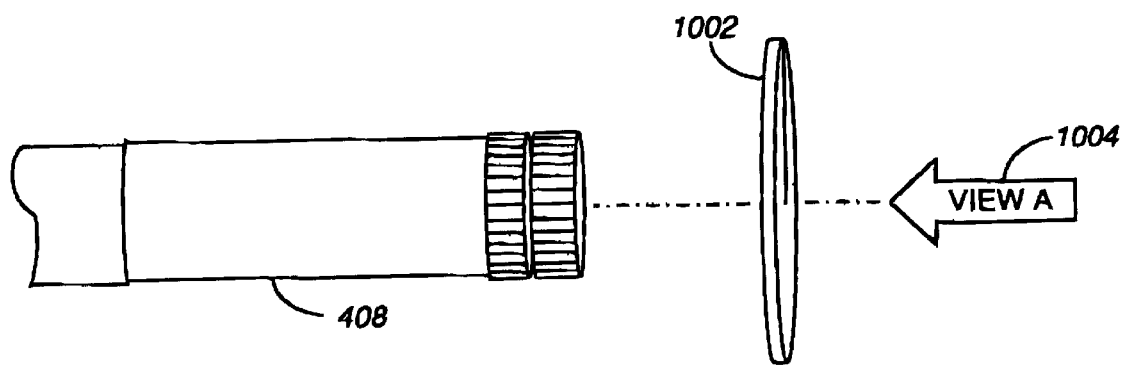
FIGS. 10–11 are diagrams showing the orientation of one C-mode image vector and a description of the initialization of the element stepping around the array necessary for the assembly of the vector in the image.
Figure 11:
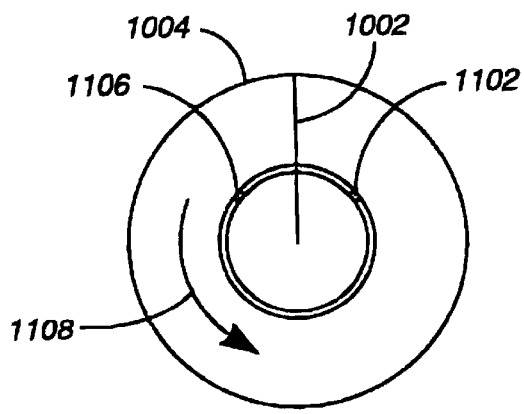

By using transmit-receive echo contributions collected from elements throughout the whole catheter array, using either a "complete data set" (e.g. 64×32), or a sparse sampling (e.g. less than 64×32) of elements as shown in FIGS. 10 and 11, the FWHM main beam resolution will be close to the 20 MHz resolution of the "side looking" cross-sectional image. This is due to the fact that although the "forward looking" echo frequency is about one half as much as the "side looking" frequency, the usable aperture for the forward looking mode is about 1.6 times that of the largest side looking aperture (i.e. the largest side looking aperture is about 0.7 mm, and the forward aperture is about 1.15 mm). For a 10 MHz forward looking design, the FWHM main lobe resolution in an image plane reconstructed at a depth of 3 mm will be approximately 0.39 mm, and 0.65 mm resolution at 5 mm distance.

Due to the limitation of beam diffraction available in the design using 10 MHz as the echo frequency for "forward looking", the C-mode image diameter that can be reconstructed and displayed with a high level of resolution from echo contributions throughout the whole array will be related to the distance between the reconstructed C-mode image plane and the distal end of the catheter. At 3 mm from the end of the catheter, the C-mode image diameter will be about 2.3 mm, at 5 mm distance the image diameter will be 4.6 mm, and at 7 mm distance the image diameter will be 6.9 mm.

The host processing system, in addition to the control of the transducer element selection and stepping around the array, will control the transmit pulse timing, the use of any matched filter to perform echo pulse compression, and the echo band pass filter processing path in the system. The amplified and processed analog echo information is digitized with enough bits to preserve the dynamic range of the echo signals, and passed to the beamformer processing section. The beam former section uses stored echo data from the sparse array sampling (or alternatively the whole complete array echo data set of 64×32 of transmit-receive element pairs) that exist in an aperture of interest. As the element echo sampling continues sequentially around the circular array 1108 as shown in FIGS. 10 and 11, a number of "full trips" around the array will have been made to collect a sufficient number of echo cross-products (up to 105 in the preferred sparse sampling method) to allow the reconstruction of one image vector line 1102. As cross-product sampling continues around the array, the "older" echo cross-product collections are replaced with new samples and the next image vector is formed. This process repeats through an angular rotation to create new image vectors while sampling their element cross-product contributors around the array.

In FIG. 11, view "A" 1004 of FIG. 10 is shown which is a superposition of the distal catheter array and the forward looking image. Transducer elements #1 and #2 shown as item 1102 show the start location for the transmit (Tx) transducer elements. Transducer elements #12 and #13 shown as item 1106 is the start location for the Rx transducer elements. To collect the echo data for vector 1002, a total of 105 cross-products will be collected from all around the array. Rotation arrow 1108 shows the direction of Rx element stepping around the array. The Rx stepping preferably stops at about element #52 (e.g., 64−12=52). The stepping continues by stepping the Rx back around after the Tx has been incremented in the same "rotate" direction. Obviously, not all cross-product Tx-Rx terms are collected. Preferably, one takes the primary spatial frequencies, and continues the collection to limit the cross-products to 105.

In the same manner as described in the processing of the "side looking" image, the vector echo data is processed through envelope detection of the echo data and rejection of the RF carrier. Finally a process of coordinate conversion is done to map the radial vector lines of echo data to raster scan data for video display.

This processing system, through the host control, may also accomplish "forward looking" target (such as blood cells) velocity detection by either correlation-tracking the targets along the "forward looking" direction (with processing as earlier discussed with the "side looking" approach), or by standard Doppler processing of echo frequency shifts that correspond to target movement in directions parallel with the "forward looking" echo paths. The target (e.g. blood) velocity information may be displayed as a color on the video display; this velocity color information is superimposed on the image display to allow the user to see simultaneous anatomical information and target movement information.

Forward Looking Sagittal-Sectional B-Mode Operation

The advantage of the "forward looking" operation of the catheter imaging device is in its ability to see an image of objects in front of the catheter where possibly the catheter could not otherwise physically traverse. "Forward" B-mode plane imaging produces a cross-sectional planar "sector" view (see FIG. 3) that can exist in any plane parallel to the catheter central axis and distal to the end of the catheter array. This imaging mode may be used, in addition, to produce image "sector" views that are tilted slightly out of plane (see FIG. 3), and as well, may produce individual or sets of image "sectors" rotated generally about the catheter axis to allow the user to see a multitude of forward image slices in a format that shows clearly the multidimensional aspects of the forward target region of interest. This forward B-mode imaging (as with C-mode plane imaging) utilizes the ideal acoustic beam positioning for the detection and color image display of Doppler echo signals from targets moving generally in parallel with the long axis of the catheter device.

1. Transducer Operation

The transducer operation in creating the "forward looking" B-mode image format is virtually the same as discussed earlier for creating the "forward looking" C-mode image. The transducer in this "secondary" mode operates in the length extensional (LE) resonance, utilizing the $k_{31}$ electromechanical coupling coefficient to describe the coupling efficiency. As with the C-mode image creation, the number of elements used at any time to form a wide beam pointing in the "forward" direction are selected to produce a required 60 degree FWHM beam width performance; the modal isolation techniques mentioned earlier against the higher frequency TE resonances are valid as well for this forward B-mode imaging method.

However, where it is merely preferred to operate the "forward" C-mode imaging with high bandwidth echo signals (low bandwidth echo signals can also be used, but with some minor loss in image resolution), it is a requirement in the "forward" B-mode imaging that only high bandwidth echo signals (echo fractional bandwidth greater than 30%) be used to preserve the "axial" resolution in the "forward" B-mode image. The lateral resolution in the "forward" B-mode image is determined (as the C-mode image plane resolution) by the aperture (diameter of the array) used for the image reconstruction. The lateral resolution performance will be as stated earlier (i.e. from the description of the C-mode imaging case) for various depths from the catheter distal end.

2. System Operation

The system operation in creating the "forward looking" B-mode image format is largely the same as discussed earlier for creating the "forward looking" C-mode image, with the difference being in the use of the echo signals collected in the beamforming process to create, rather than a C-mode image plane, a "forward" sagittal B-mode image in a plane that effectively cuts through the center of the circular array at the distal end of the catheter.

The host processing system as shown in FIG. 9, will control the array element selection and stepping process whereby one element, a two element pair, or other multiple elements in combination, will transmit and the same or other elements will receive the return echo information. The intended array operational mode is the LE resonant mode to send and receive echo information in a forward direction from the end of the catheter array. As stated earlier, the LE mode echoes produced may be isolated from the TE mode echoes through primarily frequency band limitations (both by transducer structural design and by electrical band selection filters), and through the beamforming reconstruction process itself as a kind of echo selection filter.

To produce an image of the best possible in-plane resolution while operating in the "forward looking" sagittal B-mode, the entire array diameter will be used as the maximum aperture dimension. This means that, in general, element echo sampling will take place at element locations throughout the whole array in preferably a sparse sampling mode of operation to gather the necessary minimum number of cross-product echoes needed to create image resolution of high quality everywhere in the reconstructed plane. By using transmit-receive echo contributions collected from elements throughout the whole catheter array, using either a "complete data set" (e.g. 64×32), or a sparse sampling (e.g. less than 64×32) of elements, the FWHM main beam lateral resolution in the B-mode plane will be close to the 20 MHz resolution of the "side looking" cross-sectional image. Similarly, as stated earlier for the C-mode image case, in the creation of the B-mode image using a 10 MHz forward looking design, the FWHM main lobe lateral resolution in the image plane reconstructed at a depth of 3 mm will be approximately 0.39 mm, and 0.65 mm resolution at 5 mm distance.

Due to the limitation of beam diffraction available in the design using 10 MHz as the echo frequency for "forward looking", the B-mode sector image width that can be reconstructed and displayed with a high level of resolution from echo contributions throughout the whole array will be related to the distance between the reconstructed B-mode target depth in the image sector and the distal end of the catheter. At 3 mm from the end of the catheter, the B-mode image sector width will be about 2.3 mm, at 5 mm distance the image sector width will be 4.6 mm, and at 7 mm distance the image sector width will be 6.9 mm.

The host processing system, in addition to the control of the transducer element selection and stepping around the array, will control the transmit pulse timing, the use of any matched filter to perform echo pulse compression, and the echo band pass filter processing path in the system. The amplified and processed analog echo information is digitized with enough bits to preserve the dynamic range of the echo signals, and passed to the beamformer processing section. The beam former section uses stored echo data from the sparse array sampling (or alternatively the whole complete array echo data-set of 64×32 of transmit-receive element pairs) that exist in an aperture of interest. As the element echo sampling continues sequentially around the circular array, a number of "full trips" around the array will have been made to collect a sufficient number of echo cross-products (up to 105 in the preferred sparse sampling method) to allow the reconstruction of one image vector line. As cross-product sampling continues around the array, the "older" echo cross-product collections are replaced with new samples and the next image vector is formed. This process repeats through an angular rotation in the array to create new image vectors while sampling their element cross-product contributors around the array.

The method used for the creation of a single "forward looking" sagittal B-mode image plane may be expanded to create multiple rotated sagittal planes around an axis either congruent with the catheter central axis, or itself slightly tilted off the catheter central axis. If enough rotated planes are collected, the beamforming system could then possess a capability to construct and display arbitrary oblique "slices" through this multidimensional volume, with B-mode or C-mode visualization in either a 2-D sector format, a 2-D circular format, or, other multidimensional formats. The echo data volume may also be off-loaded to a conventional 3-D graphics engine that could create the desired image format and feature rendering that would enable improved visualization. In the same manner as described in the processing of the "forward looking" C-mode image, the vector echo data is processed through envelope detection of the echo data and rejection of the RF carrier. Finally a process of coordinate conversion is done to map the radial vector lines of echo data to a video sector-format display of the "forward looking" B-mode image.

This processing system, through the host control, may also accomplish "forward looking" target (such as blood cells) velocity detection by either correlation-tracking the targets along the "forward looking" direction (with processing as earlier discussed with the "side looking" approach), or by standard Doppler processing of echo frequency shifts that correspond to target movement in directions parallel with the "forward looking" echo paths in the "forward looking" B-mode plane. The target (e.g. blood) velocity information may be displayed as a color on the video display; this velocity color information is superimposed on the image display to allow the user to see simultaneous anatomical information and target movement information.

The invention has a number of important features and advantages. It provides an ultrasonic imaging transducer and method that can be used for imaging tissue in multiple planes without any moving parts. It can operate in both forward and side imaging modes, and it permits imaging to be done while procedures are being carried out. Thus, for example, it can operate in a forward looking C-mode, while at the same time a therapeutic device such as a laser fiber-bundle can be used to treat tissue (e.g. an uncrossable arterial occlusion) ahead of the catheter tip either by tissue ablation, or, tissue photochemotherapy. The laser pulses may be timed with the ultrasound transmit-receive process so that the high frequency laser induced tissue reverberations can be seen in the ultrasound image plane simultaneously. In this way the invention can dynamically guide the operator's vision during a microsurgical procedure.

The present invention can also be used in a biopsy or atherectomy procedure to allow the operator to perform a tissue identification prior to tissue excision; the advantage being that the catheter or biopsy probe device can be literally pointing in the general direction of the target tissue and thus aid significantly in the stereotaxic orientation necessary to excise the proper tissue sample. The invention can also be used for the proper positioning of a radiotherapy core wire in the treatment of target tissue that exists well beyond the distal extent of the catheter.

It is apparent from the foregoing that a new and improved ultrasonic imaging device and method have been provided. While only certain presently preferred embodiments have been described in detail, as will be apparent to those familiar with the art, certain changes and modifications can be made without departing from the scope of the invention as defined by the following claims.

What is claimed is:

1. An ultrasonic imaging device, comprising:
   a plurality of transducer elements arranged in a circular array about an axis, each of the elements comprising a body of piezoelectric material having a thickness dimension perpendicular to the axis and a length dimension parallel to the axis; and
   means for selectively exciting the transducer elements at a first resonant frequency having a half wavelength equal to the thickness dimension and at a second resonant frequency having a half wavelength equal to the length dimension.

2. The ultrasonic imaging device of claim 1, wherein the length dimension is on the order of twice the thickness dimension and the first resonant frequency is on the order of twice the second resonant frequency.

3. The ultrasonic imaging device of claim 1, wherein the body of each transducer element has a transversely extending notch toward one end thereof, with a wall of the notch being perpendicular to the axis, and the length dimension of the body being the distance between the one end and the wall.

4. The ultrasonic device of claim 3, wherein the notch has a generally triangular profile in cross-section.

5. The ultrasound imaging device of claim 3 wherein the notch is filled with a low acoustic impedance material.

6. The ultrasonic imaging device of claim 1, further including an acoustic matching tube disposed coaxially within the cylindrical substrate, and a body of acoustic absorbing material between the plurality of transducer elements and the tube.

7. The ultrasound imaging device of claim 6, further including a radiopaque marker disposed between the acoustic matching tube and the acoustic absorbing materials.

8. The ultrasound imaging device of claim 1, wherein the plurality of transducer elements are formed from a generally rectangular body of piezoelectric material mounted upon a flexible circuit substrate, then making a series of lengthwise cuts forming individual ones of the plurality of transducer elements, and then forming the flexible substrate into a substantially cylindrical shape.

9. The ultrasound imaging device of claim 8 wherein the means for selectively exciting the transducer elements comprise integrated circuits mounted upon the flexible substrate.

10. The ultrasonic imaging device of claim 1 wherein ones of the plurality of transducer elements have first and second portions separated by an acoustical discontinuity.

11. The ultrasound imaging device of claim 1 further comprising a flexible substrate.

12. The ultrasound imaging device of claim 1 wherein ones of the plurality of transducer elements are poled in one direction along an entire length of the transducer elements.

13. The ultrasound imaging device of claim 12 wherein ones of the plurality of transducer elements are sized to resonate in a thickness extension mode and a length extension mode.

14. The ultrasound imaging device of claim 13 wherein a resonant frequency for the thickness extension mode is about 1.5 to 2 times a resonant frequency for the length extension mode.

15. The ultrasound imaging device of claim 1 wherein the plurality of transducer elements are arranged to facilitate forming, from signals produced by the transducer elements, images in a B-mode lateral plane that is perpendicular to the axis of the circular array and passes trough the transducer elements, a B-mode forward plan that extends in a forward direction from the transducers at an arbitrary angle with respect to the axis of the circular array, and a C-mode plane that is perpendicular to the axis of the circular array and spaced in front of the transducers.

16. A method of ultrasonic imaging, comprising the steps of:

arranging a plurality of transducer elements in a circular array about an axis, with each of the elements having a body of piezoelectric material with a thickness dimension perpendicular to the axis and a length dimension parallel to the axis, and selectively exciting the transducer elements at a first resonant frequency having a half wavelength equal to the thickness dimension and at a second resonant frequency having a half wavelength equal to the length dimension.

17. The method of claim 16, wherein the length dimension is selected to be on the order twice the thickness dimension and the first resonant frequency is on the order of twice the second resonant frequency.

18. The method of claim 16, including the further step of:

forming a transversely extending notch toward one end of the body of each transducer element, with a wall of the notch being perpendicular to the axis, and the length dimension of the body being the distance between the one end and the wall.

19. The method of claim 18, wherein the notch is formed to have a generally triangular profile in cross-section.

20. The method of claim 16 wherein the selectively exciting step facilitates forming, from signals produced by the transducer elements, images in a B-mode lateral plane that is perpendicular to the axis of the circular array and passes through the transducer elements, a B-mode forward plan that extends in a forward direction from the transducers at an arbitrary angle with respect to the axis of the circular array, and a C-mode plane that is perpendicular to the axis of the circular array and spaced in front of the transducers.

21. The method of claim 16 wherein the first resonant frequency is about 1.5 to 2 times the second resonant frequency.

22. A method of ultrasonic imaging, for an ultrasonic imaging system including an ultrasound imaging device having a plurality of transducer elements in a circular array about an axis, with each of the elements having a body of piezoelectric material with a thickness dimension perpendicular to the axis and a length dimension parallel to the axis, tic method comprising the steps of:

selectively exciting the transducer elements at a first resonant frequency having half wavelength equal to the thickness dimension and at a second resonant frequency having a half wavelength equal to the length dimension.

23. The method of claim 22 wherein the selectively exciting step facilitates forming, from signals produced by the transducer elements, images in a B-mode lateral plane that is perpendicular to the axis of the circular array and passes through the transducer elements, a B-mode forward plan that extends in a forward direction from the transducers at an arbitrary angle with respect to the axis of the circular array, and a C-mode plane that is perpendicular to the axis of the circular army and spaced in front of the transducers.

24. The method of claim 22 wherein the first resonant frequency is about 1.5 to 2 times the second resonant frequency.

25. The method of claim 22 wherein the transducer elements are operated in a thickness extension mode for transmitting and receiving ultrasonic energy in a direction perpendicular to the axis of the catheter and in a length extension mode for transmitting and receiving energy along the axis.

26. The method of claim 25 wherein the transducer elements are excited at a first resonant frequency for the thickness extension mode and at a second resonant frequency for the length extension mode.

27. The method of claim 26 wherein the first resonant frequency for the thickness extension mode is about 1.5–2.0 times the second resonant frequency for the length extension mode.

* * * * *